(12) United States Patent
Karpf et al.

(10) Patent No.: US 11,009,459 B2
(45) Date of Patent: May 18, 2021

(54) FAST TWO-PHOTON IMAGING BY DIFFRACTED SWEPT-LASER EXCITATION

(71) Applicants: THE REGENTS OF THE UNIVERSITY OF CALIFORNIA, Oakland, CA (US); UNIVERSITAET ZU LUEBECK, Luebeck (DE)

(72) Inventors: Sebastian Karpf, Los Angeles, CA (US); Bahram Jalali, Los Angeles, CA (US); Robert Huber, Luebeck (DE)

(73) Assignees: THE REGENTS OF THE UNIVERSITY OF CALIFORNIA, Oakland, CA (US); UNIVERSITAET ZU LUEBECK, Luebeck (DE)

( * ) Notice: Subject to any disclaimer, the term of this patent is extended or adjusted under 35 U.S.C. 154(b) by 176 days.

(21) Appl. No.: 16/233,242

(22) Filed: Dec. 27, 2018

(65) Prior Publication Data

US 2019/0226989 A1 Jul. 25, 2019

Related U.S. Application Data

(63) Continuation of application No. PCT/US2017/039705, filed on Jun. 28, 2017.
(Continued)

(51) Int. Cl.
*G01N 21/64* (2006.01)
*H01S 3/067* (2006.01)
(Continued)

(52) U.S. Cl.
CPC ....... *G01N 21/6402* (2013.01); *A61B 5/0071* (2013.01); *A61B 5/0075* (2013.01);
(Continued)

(58) Field of Classification Search
CPC ............... G01N 21/6402; G01N 21/00; G01N 21/6408; G01N 2201/06113;
(Continued)

(56) References Cited

U.S. PATENT DOCUMENTS

| 2,671,182 A | 3/1954 | Havens |
| 5,793,907 A | 8/1998 | Jalali |

(Continued)

FOREIGN PATENT DOCUMENTS

| WO | 2014180983 A1 | 11/2014 |
| WO | 2014180986 A1 | 11/2014 |

(Continued)

OTHER PUBLICATIONS

ISA/US, United States Patent and Trademark Office (USPTO), International Search Report and Written Opinion dated Sep. 8, 2017, related PCT international application No. PCT/US2017/039705, pp. 1-10, claims searched, pp. 11-14.

(Continued)

*Primary Examiner* — Blake C Riddick
(74) *Attorney, Agent, or Firm* — O'Banion & Ritchey LLP; John P. O'Banion

(57) ABSTRACT

An apparatus and methods for high-speed non-linear spectrally encoded multi-photon imaging that are particularly suited for use in two photon fluorescence and fluorescence lifetime imaging. The system is capable of optical image compression and scale invariant digital zoom. A wavelength agile laser with digitally synthesized electro-optic modulation in a master oscillator-power amplifier configuration is combined with spectral encoding to eliminate the speed limitations of inertial scanning. The technique for fast two photon fluorescent imaging with simultaneous lifetime imaging independently detects the location, amplitude and lifetime of fluorescent emission by synthesizing a sequential (Continued)

excitation beam via digital electro-optic modulation of a quasi-CW swept source followed by time encoded detection. For fluorescent imaging, spectral and temporal mappings are employed separately, with quasi-CW spectral encoding used for pumping and time encoding for constructing the image at fluorescence wavelength.

27 Claims, 2 Drawing Sheets

Related U.S. Application Data

(60) Provisional application No. 62/355,571, filed on Jun. 28, 2016.

(51) Int. Cl.
  *H01S 3/00* (2006.01)
  *G02B 21/00* (2006.01)
  *H01S 3/083* (2006.01)
  *A61B 5/00* (2006.01)
  *G01N 21/00* (2006.01)
  *H01S 3/13* (2006.01)
  *H01S 5/14* (2006.01)
  *H01S 3/16* (2006.01)
  *H01S 5/50* (2006.01)

(52) U.S. Cl.
  CPC ......... *G01N 21/00* (2013.01); *G01N 21/6408* (2013.01); *G02B 21/0076* (2013.01); *G02B 21/0084* (2013.01); *H01S 3/0071* (2013.01); *H01S 3/0085* (2013.01); *H01S 3/06758* (2013.01); *H01S 3/083* (2013.01); *H01S 3/1305* (2013.01); *H01S 5/146* (2013.01); *G01N 2201/0696* (2013.01); *G01N 2201/06113* (2013.01); *G01N 2201/1053* (2013.01); *H01S 3/06712* (2013.01); *H01S 3/1618* (2013.01); *H01S 5/50* (2013.01)

(58) Field of Classification Search
  CPC .... G01N 2201/0696; G01N 2201/1053; A61B 5/0071; A61B 5/0075; G02B 21/0076; G02B 21/0084; H01S 3/0071; H01S 3/0085; H01S 3/06758; H01S 3/083; H01S 3/1305; H01S 3/06712; H01S 3/1618; H01S 5/146; H01S 5/50
  See application file for complete search history.

(56) References Cited

U.S. PATENT DOCUMENTS

| | | | | |
|---|---|---|---|---|
| 6,687,000 | B1* | 2/2004 | White | G01N 21/6408 356/300 |
| 7,535,631 | B2 | 5/2009 | Brown | |
| 7,916,387 | B2 | 3/2011 | Schmitt | |
| 7,991,022 | B1 | 8/2011 | Soh | |
| 8,665,918 | B2 | 3/2014 | Creeden | |
| 9,634,454 | B1* | 4/2017 | Kieu | G02B 21/002 |
| 2004/0233944 | A1* | 11/2004 | Dantus | G01B 9/02091 372/25 |
| 2006/0056468 | A1* | 3/2006 | Dantus | G01B 9/02014 372/28 |
| 2010/0141829 | A1* | 6/2010 | Jalali | G01B 9/02028 348/370 |
| 2010/0296531 | A1 | 11/2010 | Hohm | |
| 2014/0218726 | A1* | 8/2014 | Cheng | G01J 3/02 356/301 |
| 2014/0268168 | A1 | 9/2014 | Feldman | |
| 2014/0285873 | A1* | 9/2014 | Kieu | H01S 3/2391 359/329 |
| 2016/0091429 | A1 | 3/2016 | Huber | |
| 2016/0238532 | A1* | 8/2016 | Freudiger | G01N 21/6402 |

FOREIGN PATENT DOCUMENTS

| | | |
|---|---|---|
| WO | 2015185620 A1 | 12/2015 |
| WO | 2016038461 A2 | 3/2016 |
| WO | 2018005623 A1 | 1/2018 |

OTHER PUBLICATIONS

Iwamoto, Kyohei et al., "Two-dimensional image transmission based on the ultrafast optical data format conversion between a temporal signal and a two-dimensional spatial signal", Applied Optics, vol. 40, No. 35, pp. 6527-6534, Dec. 10, 2001.
Tearney, G. J. et al., "Spectrally encoded confocal microscopy", Optics Letters, 23, 1152-1154, 1998.
Hwang, J. et al., "Frequency- and spectrally-encoded confocal microscopy", Optics Express, 23, 5809-5821, 2015.
Goda, K. et al., "Serial time-encoded amplified imaging for real-time observation of fast dynamic phenomena", Nature, 458, 1145-1149, 2009.
Huber, R. et al., "Fourier domain mode locking at 1050 nm for ultra-high-speed optical coherence tomography of the human retina at 236,000 axial scans per second", Optics Letters, 32, 2049-2051, 2007.
Huber, R. et al., "Fourier Domain Mode Locking (FDML): A new laser operating regime and applications for optical coherence tomography", Optics Express, 14, 3225-3237, 2006.
Klein T. et al., "Multi-MHz retinal OCT", Biomedical Optics Express, 4, 1890-1908, 2013.
Wieser, W. et al., "Multi-Megahertz OCT: High quality 3D imaging at 20 million A-scans and 45 GVoxels per second", Optics Express, 18, 14685-14704, 2010.
Wieser, W. et al., "Dispersion Compensated Megahertz FDML Laser for Imaging of the Anterior Segment", in Conference on Lasers and Electro-Optics 2012. 2012. San Jose, California: Optical Society of America.
Biedermann, B.R. et al., "Dispersion, coherence and noise of Fourier domain mode locked lasers", Optics Express, 17, 9947-9961, 2009.
Xu, C. et al., "Measurement of two-photon excitation cross sections of molecular fluorophoreswith data from 690 to 1050 nm", Journal of the Optical Society of America B, 13, 481-491, 1996.
fluorophores.org—Database of fluorescent dyes, properties and applications. Apr. 7, 2015]; Available from: http://www.fluorophores.tugraz.at.
Huber, R. et al., "Buffered Fourier domain mode locking: unidirectional swept laser sources for optical coherence tomography imaging at 370,000 lines/s", Optics Letters, 31, 2975-2977, 2006.
Karpf, S. et al., "A Time-Encoded Technique for fibre-based hyperspectral broadband stimulated Raman microscopy", Nature Communications, 6, 6784, 2015.
Stolen, R.H. et al., "Raman gain in glass optical waveguides", Applied Physics Letters, 22, 276-278, 1973.
Jayaraman, V. et al., "OCT Imaging up to 760Khz Axial Scan Rate Using Single-Mode 1310nm MEMs-Tunable VCSELs with >100nm Tuning Range", in CLEO:2011—Laser Applications to Photonic Applications. 2011. Baltimore, Maryland: Optical Society of America.
Grulkowski I. et al., "High-precision, high-accuracy ultralong-range swept-source optical coherence tomography using vertical cavity surface emitting laser light source", Optics Letters, 38, 673-675, 2013.
Yun, S.H. et al., "High-speed wavelength-swept semiconductor laser with a polygon-scanner-based wavelength filter", Optics Letters, 28, 1981-1983, 2003.
Tsai, T.-H. et al., "Frequency comb swept lasers", Optics Express, 17, 21257-21270, 2009.

(56) References Cited

OTHER PUBLICATIONS

Eigenwillig, C.M. et al., "K-space linear Fourier domain mode locked laser and applications for optical coherence tomography", Optics Express, 16, 8916-8937, 2008.

Hu, Z. et al. "Fourier domain optical coherence tomography with a linear-in-wavenumber spectrometer", Optics Letters, 32, 3525-3527, 2007.

* cited by examiner

FAST TWO-PHOTON IMAGING BY DIFFRACTED SWEPT-LASER EXCITATION

CROSS-REFERENCE TO RELATED APPLICATIONS

This application claims priority to, and is a 35 U.S.C. § 111(a) continuation of, PCT international application number PCT/US2017/039705 filed on Jun. 28, 2017, incorporated herein by reference in its entirety, which claims priority to, and the benefit of, U.S. provisional patent application Ser. No. 62/355,571 filed on Jun. 28, 2016, incorporated herein by reference in its entirety. Priority is claimed to each of the foregoing applications.

The above-referenced PCT international application was published as PCT International Publication No. WO 2018/005623 A1 on Jan. 4, 2018, which publication is incorporated herein by reference in its entirety.

STATEMENT REGARDING FEDERALLY SPONSORED RESEARCH OR DEVELOPMENT

This invention was made with Government support under Grant number GM107924, awarded by the National Institutes of Health. The Government has certain rights in the invention.

INCORPORATION-BY-REFERENCE OF COMPUTER PROGRAM APPENDIX

Not Applicable

BACKGROUND

1. Technical Field

The technology of this disclosure pertains generally to laser scanning imaging systems and methods, and more particularly to high-speed non-linear imaging systems and methods for two photon fluorescence and fluorescence lifetime imaging (FLIM). The methods include a Two-Photon Spectro-temporal Lifetime Imaging by Digitally sculpted Excitation (SLIDE) technique.

2. Background Discussion

Nonlinear optical techniques and in particular two photon excited fluorescence imaging have emerged as powerful tools for deep tissue imaging with sub-cellular resolution, brain mapping and 3D printing. At the same time, fluorescent lifetime imaging can probe the internal biochemical interactions and external environment of a molecule useful for DNA sequencing, the detection of tumour margins necessary for successful surgical removal, and quantifying cellular energy metabolism in living cells. To image fast dynamic processes such as biological cells in flow or neural activities, these methods must provide frame rates beyond 1000 Hz. However, achieving high speed is challenged by lower efficiency of nonlinear vs. linear processes requiring illumination with a high-intensity tightly-focused beam that is scanned over sample area. The scanning is typically done with mechanical scanners, the speed of which limits the frame rate. Acousto-optic scanners provide an intermediate solution; however, the frame rate is limited by the acoustic velocity leading to a trade-off between resolution and speed.

Two Photon Microscopy enables deep tissue imaging at high resolution. Since its introduction, a main interest of research has been increasing the imaging speed above 1 kHz in order to observe millisecond dynamics of neural activity and to avoid artefacts in a moving target. In Two-Photon Microscopy, the required excitation power depends on illumination intensity squared. This quadratic dependency favours beam-steering over wide-field illumination leading to the popular use of galvanometric scanning mirrors. Such mechanically scanning mirrors are inertia-limited and too slow for 2-D frame-rates in the biologically important kHz range. Fast imaging speeds are also desired for superior signal generation performance.

Different approaches for overcoming the inertia-limit of mechanical scanners have been investigated, with the most prominent employing either acousto-optic deflectors (AOD) or parallelizing the excitation by employing multiple beams. However, these approaches have added complexity, require dispersion management and lack high timing resolution. The finite latency associated with the propagation velocity of the acoustic wave through the acousto-optic interaction volume causes an ambiguity in the diffraction angle leading to reduced spatial resolution at high scanning rates. This trade-off between resolution and speed is a fundamental known limitation of AOD technology. Also, it is difficult to augment AOD scanning with fibre delivery, which is crucial for endoscopic applications.

Spectral-Encoded scanning increases imaging speeds by spectrum-to-space mapping and has been employed for confocal microscopy. Photonic time stretch is a high speed data acquisition method that combined with spectral scanning leads to single shot acquisition of bright field images with record speed.

Interferometric time stretch techniques achieving fast phase sensitive imaging have been combined with artificial intelligence to produce successful label-free classification of cancer cells in blood in a microfluidic channel. In time stretch microscopy, both the spectrum and the time are needed to identify the pixel location through spectrum to time mapping. Extension of time stretch to fluorescence imaging has been hindered because both the emission spectrum and fluorescent lifetime are governed by the molecule which is independent of spectrum-to-time mapping.

To enable fast fluorescent imaging, the radio frequency (RF) encoded excitation (FIRE) technique has been developed. The RF domain is utilized instead of the optical spectrum for spatial encoding enabling multi-KHz frame rate single photon fluorescent imaging. The technique can also perform rapid single-pixel lifetime measurements but not rapid lifetime imaging. Extension of FIRE to two photon imaging is difficult because an entire line scan is illuminated simultaneously resulting in insufficient optical intensity for excitation of two photon processes.

Accordingly, there is a need for systems and methods of laser scanning imaging with high imaging rates for capturing fast biological and chemical processes.

BRIEF SUMMARY

The present technology provides high-speed, non-linear imaging system and methods for spectrally encoded multi-photon imaging that are particularly suited for two photon fluorescence and fluorescence lifetime imaging (FLIM). The methods include a Two-Photon Spectro-temporal Lifetime Imaging by Digitally sculpted Excitation (SLIDE) technique to enable fast two photon fluorescent imaging with simultaneous lifetime imaging. This technique independently detects the location, the amplitude and the lifetime of fluorescent emission, a capability that is not available with known spectral and RF-encoding and time stretch techniques. This is accomplished by synthesizing a sequential excitation beam via digital electro-optic modulation of a quasi-CW swept agile laser light source followed by time encoded detection. To enable fluorescent imaging, spectral and temporal mappings are employed separately, with quasi-CW spectral encoding used for pumping and time encoding for constructing the image at fluorescence wavelengths.

In one embodiment, the sample consists of a flow apparatus where objects pass the optical beam in flow and imaging is performed of the objects in the flow. For example, the flowing sample may be blood flow, either in vivo or ex vivo. The fluorescence lifetime can be imaged and recorded for each pixel and hence a fluorescence lifetime image can be obtained of the objects in flow.

The system preferably utilizes a rapid wavelength-swept Fourier-Domain Mode-Locked (FDML) laser with digitally synthesized electro-optic modulation in a master oscillator-power amplifier configuration that is combined with spectral encoding to eliminate the speed limitations of inertial scanning in the art and to achieve single-shot imaging. However, the light source does not need to sweep. It can be dynamically switched to operate also in stationary mode or substantially different speeds/patterns.

The present system demonstrates lifetime imaging with 2 kHz frame-rate (88 MHz pixel rate) that greatly exceeds the capability of existing FLIM and two-photon FLIM systems. The system also provides optical image compression via spatially-warped two photon excitation and scale invariant digital zoom. This method allows nonlinear imaging flow cytometry, rapid recording of neuronal activity and mapping of non-repetitive biomolecular dynamics at a sub-cellular optical resolution. Since the apparatus is fiber based, the methods can be used for endoscopic medical applications.

By way of example, and not of limitation, a passive scanning mechanism is employed to circumvent the inertia limit of current mechanical scanning systems. The principle is similar to the technique used in serial time-encoded amplified microscopy (STEAM) imaging, where a broadband light source is diffracted by a grating in order to produce a spectral brush on the sample. Thus, a whole line can be covered very rapidly. However, in STEAM the whole line is imaged simultaneously, which would not work for two-photon excited fluorescence (TPEF) imaging. In TPEF, all pixel responses would have the same spectral color and thus cannot be separated by a dispersive element such as the commonly used dispersive optical fiber. In contrast, this invention uses a rapidly wavelength swept laser (e.g. an FDML laser) in combination with a diffractive element such as a diffraction grating, to disperse the wavelength sweep onto a line. In order to generate the non-linear signal, the laser light may be modulated to short pulses and amplified to high instantaneous powers. This way, each pulse corresponds to a pixel and the generated signals from a sample can be recorded by a single photodetector, sequentially in time for each pixel. The concept is illustrated in FIG. 1.

A wavelength swept laser or other suitable wavelength agile laser outputs a periodical sweep in wavelength. Each sweep is modulated to a number n of pulses and amplified to high instantaneous powers. This way the average power is the product of duty cycle and instantaneous power. The laser is preferably built using single-mode optical fiber, most preferably using a polarization maintaining fiber. The output of this pulsed-amplified swept laser is sent onto a diffraction grating. Each pulse is diffracted at a different angle, according to its wavelength, and is focused to different positions on the sample. The line scanning rate is thus the wavelength sweeping rate of the laser, which is in the order of kHz to MHz. A 2-dimensional image can be achieved with a second scanning device, e.g. a galvanometric mirror. Each pixel has a well-defined time and thus can be recorded with a single photodetector.

In one embodiment, the pulsed excitation light generates fluorescence, which is separated from the excitation light via a dichroic filter. The light is then sent to a photomultiplier tube (PMT). The generated electrical signal is proportional to the fluorescence signal and is digitized by an analog-to-digital converter (ADC). Each pixel is illuminated individually and sequentially in time; thus, each fluorescence signal is digitized serially and a one-to-one mapping of the detected signals to the pixels of an image is possible.

In one embodiment, an appropriate dichroic filter separates the generated signal (SHG, THG, TPEF etc.) from the excitation light. The non-linear signal is detected on a fast photomultiplier and digitized at high speed. Each pixel is thus recorded sequentially and no pixel cross-talk occurs.

The imaging speed of the present multi-photon system is given by the speed of the slow-axis scanning device. Here, resonant galvanometric mirrors can be used to achieve frame-rates of 1-40 kHz. This means, that the slow-axis (scanner) can have speeds of the fast-axis of today's state-of-art multi-photon systems, resulting in orders of magnitude faster non-linear imaging speeds.

The active modulation of the pulses allows the user to flexibly choose the pulse length, pulse form, pulse pattern, repetition rate, non-repetitive pulse patterns, pulse height, powers, wavelengths etc, as the employed MOPA architecture is known to be a very flexible system for various illumination conditions.

It can be seen that the fast lifetime imaging capability is possible by the direct analogue recording of the fluorescent lifetime decay and is further enhanced by the higher number of photons generated per pulse by picosecond excitation pulses, enabling single pulse per pixel illumination. This has a number of advantages over traditional illumination: (i) A single pulse per pixel leads to a very low effective repetition rate per pixel, equal to the frame-rate (approximately 2 kHz). This has been shown to decrease photobleaching and thereby increasing the signal levels. (ii) Longer pulses lead to reduced pulse peak powers at same SNR, thus having the advantage of avoiding higher-than-quadratic effects like photobleaching and photodamage (scale at orders>2). (iii) The longer pulses are generated by digitally synthesized EO modulation which renders the excitation pattern freely programmable. For example, for optimal detection the pixel rate can be tailored to the fluorescence lifetime of the sample and allows warped (anamorphic) spatial illumination that takes advantage of sparsity to achieve optical data compression. (iv) Longer pulses generate quasi-monochromatic light and this renders the high-speed line-scanning spectral mapping by diffraction gratings possible. (v) The quasi-monochromatic light is optimally compatible with fiber delivery by omitting chromatic dispersion and pulse spreading. The excitation laser presented here is already fully fiber-based, making a future implementation into a multi-photon endoscope straight forward.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawings which are for illustrative purposes only.

DETAILED DESCRIPTION

Figure 1:
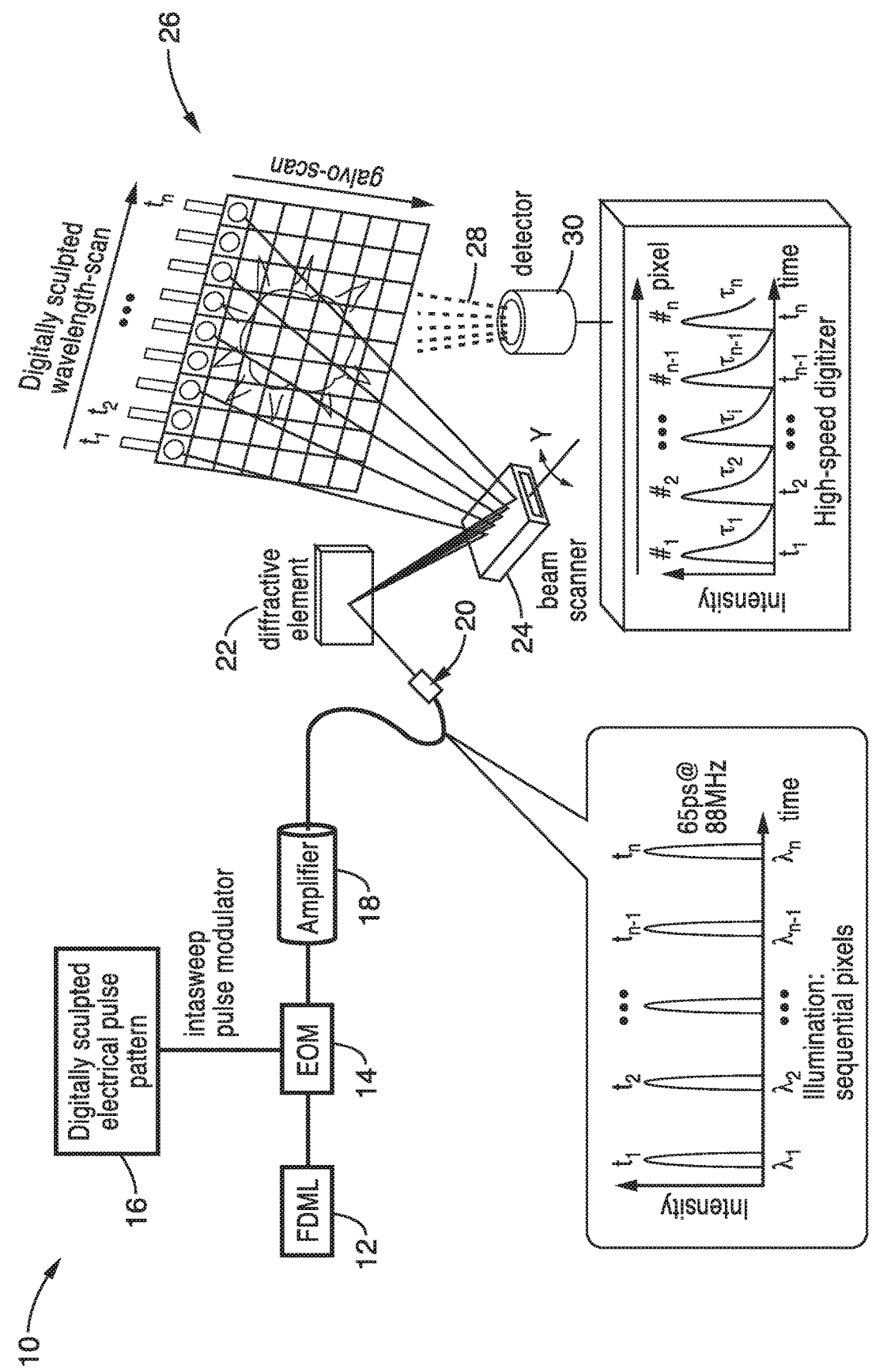
FIG. 1 is a functional block diagram a system for fast two-photon imaging by diffracted swept laser excitation according to one embodiment of the technology.

Referring more specifically to the drawings, for illustrative purposes, embodiments of the apparatus and methods for fast two-photon imaging by swept-laser excitation are generally shown. Referring more specifically to the drawings, for illustrative purposes, embodiments of methods for pathogen nucleic acid purification and identification are generally shown. Several embodiments of the technology are described generally in FIG. 1 and FIG. 2 to illustrate the apparatus and system characteristics and functionality. It will be appreciated that the methods may vary as to the specific steps and sequence and the systems and apparatus may vary as to structural details without departing from the basic concepts as disclosed herein. The method steps are merely exemplary of the order that these steps may occur. The steps may occur in any order that is desired, such that it still performs the goals of the claimed technology.

The apparatus for laser scanning generally includes a wavelength agile laser capable of generating a multi-color light source; a modulator configured for modulating the broadband light source into a dynamic time pattern and optionally an optical amplifier for amplifying the output to instantaneous powers preferably higher than the average power; and a diffractive element configured for diffracting said wavelength agile light onto a sample, wherein different wavelengths are preferentially diffracted at different angles.

The apparatus may also have a high numerical aperture for focusing, a detector and a computer controller with an imager and recorder. The interaction of the laser that is recorded can be one or more of the following interactions: absorption, non-linear absorption, reflection, scattering, ionization, plasma formation, polymerization, lithography, ablation, spectroscopy, and laser induced breakdown spectroscopy etc. In one embodiment of the apparatus, a fast detection system is employed to record the laser interactions with the sample. The interactions may be used to generate an image of the sample. The size of the obtained image can also be traded off for faster imaging speed by intelligently covering only an area of interest. In addition, the temperature of at least some of the elements of the apparatus may be controlled to achieve optimal performance.

The broadband light source is preferably a wavelength agile laser that contains an optical fiber, preferably single-mode optical fiber. A wavelength agile laser is one that can be rapidly scanned through a broad range of wavelengths. In one embodiment, an electronic differentiator can be used to achieve short impulses of an electronic step function. These short impulses can be used to modulate short impulses out of the light source.

The illumination pattern can be dynamically adapted by the wavelength output of the agile laser and/or the modulation pattern and/or an adjustable diffractive element. For example, the wavelength agile laser source can induce a pixel wise interaction with the sample and may produce multiple beam spots that are employed in parallel.

The dynamic time pattern produced by the modulator is preferably digitally programmable. In one embodiment, the dynamic time pattern encodes the diffraction pattern. In another, the dynamic time pattern employs short impulses. The individual pulse length and/or the repetition rate and/or the pulse pattern and/or individual pulse height and/or individual pulse form can be adjusted by a controller. In another embodiment, the pulse modulator comprises stimulated Raman scattering (SRS) which provides both pulse modulation and amplification.

Preferably, the spectrum of the wavelength agile laser is diffracted to achieve a spectral brush on the sample. In one embodiment, one or more secondary scanning devices are employed in order to move the spectral brush across the sample to achieve a two-dimensional or three-dimensional excitation of the sample. In one embodiment, a chromatic aberration of the focusing lens can be harnessed to achieve a depth scanning spectral brush in the sample. In addition, the multi-color output can also be harnessed to achieve a color-dependent depth scan of the sample.

In one embodiment, a nonlinear interaction is induced at the sample. For example, the non-linear interaction can be the simultaneous absorption of two or more photons in the sample. In another embodiment, the sweeping bandwidth of the excitation laser can be adjusted such that the effective bandwidth after non-linear interaction lies within the absorption band of the sample. For example, the time resolution can be high enough to observe a fluorescence lifetime decay and/or the temporal dynamic of a harmonic generation signal. The repetition rate can be adjusted to respect long fluorescence lifetimes of the sample and/or respect long-lived triplet states of the sample.

In one embodiment, the wavelength swept laser is equipped with a buffering mechanism. The buffering mechanism can provide an almost linear sweep in wavelength. This aims at allowing a linear mapping of the diffracted wavelength onto the sample. The spectral width of the wavelength agile light source can also be used to modify the scanning angle after the diffractive element.

In one embodiment of the system, the wavelength swept laser is operated with an electronic waveform, such that an almost linear sweep in wavelength is created. In an alternative embodiment, an almost linear sweep in frequency (k-space linear sweep) can be obtained. For example, the pulse modulation can be programmed to digitally set the mapping along the spectral scan on the sample. One preferential application is an unequal sampling in time in order to generate a linear spatial mapping on the sample. In one embodiment, a digitally sculpted waveform is employed to the pulse modulation to achieve non-uniform sampling on the sample. This can be used for image compression by allotting higher sampling density to a particular region of interest and less dense sampling in the periphery.

In one embodiment, an electro-optical element is used for time modulation. For example, a time-dependent bias voltage can be applied to the electro-optical element to match the wavelength dependent bias voltage to the instantaneous color output of the wavelength agile laser.

In another embodiment, the detection is driven synchronously to the pulse modulation, so as to detect only signals generated synchronous to the applied pulses and suppressing background signals. In another embodiment, the modulation system is operated with both a pulse pattern and an additional swept pattern, such as to improve the modulation depth of the pulses.

Accordingly, the multitude of generated signals can be separated based on time and/or spectral characteristic in order to multiplex the different signals for multi-modal imaging.

Generally, a new tool for high-speed non-linear imaging is provided with utility in two photon fluorescence and fluorescence lifetime imaging (FLIM) is used to illustrate the technology. To enable fast two photon fluorescent imaging with simultaneous lifetime imaging, a technique called Two-Photon Spectro-temporal Lifetime Imaging by Digitally sculpted Excitation (SLIDE) is provided. The technique independently detects the location, the amplitude and the lifetime of fluorescent emission by synthesizing a sequential excitation beam via digital electro-optic modulation of a quasi-CW swept source followed by time encoded detection. To enable fluorescent imaging, spectral and temporal mappings are employed separately, with quasi-CW spectral encoding used for pumping and time encoding for constructing the image at fluorescence wavelength.

Although the methods are demonstrated with a wavelength-swept Fourier-Domain Mode-Locked (FDML) laser with digitally synthesized electro-optic modulation in a master oscillator-power amplifier configuration combined with spectral encoding, other laser sources and configurations can be adapted to the system to perform imaging.

Turning now to FIG. 1, a system diagram of one embodiment of apparatus 10 for Two-Photon Spectro-temporal Lifetime Imaging by Digitally sculpted Excitation (SLIDE) imaging is shown schematically. Initially, an apparatus is provided with a swept-source Fourier Domain Mode-Locked (FDML) laser source 12 that is pulse-modulated with an electro-optic modulator (EOM) 14 and amplified with an optional amplifier 18. The mapping pattern 16 is digitally sculpted through the pulse modulation.

The FDML laser 12 provides a high spectro-temporal bandwidth $M_{ST}$. This is the product of the spectral span ($\Delta\lambda$) required for high-resolution imaging and the line-scan speed $\Delta T$, which is governed by the fluorescence decay times and the pixel number.

The amplified mapping pattern that has been digitally sculpted through the pulse modulation beam output 20 is diffracted by a diffractive element 22. The y-axis is scanned by a beam scanner 24 to produce rapid beam steering through spectrum-to-line mapping. In SLIDE, each pulse 20 has both a unique wavelength and time leading to a sequential and pixel wise illumination.

After fluorescence excitation 28 from the scan 26, the fluorescence 28 is detected by a detector and digitizer 30. The mapping allows both straightforward image generation and recording of the fluorescent lifetimes using a high-speed digitizer 30. The photodetector 30 may have high quantum efficiency and/or high optical and/or electrical bandwidth. The detector 30 may be of the group including an avalanche photodetector, a photomultiplier tube, a hybrid photodetector, a multichannel plate, a charged coupled detector, a CMOS detector, an arrayed detector, a gated detector, and an image intensifier and the like.

A typical excitation pulse length is 65 ps at 88 MHz repetition rate with peak power ranging from 1.8 W to 18 W and an average power in the range of 10 mW to 100 mW (pulse energies of 0.12 nJ to 1.2 nJ).

Spectro-temporal Lifetime Imaging places rigorous requirements on the time-bandwidth of the optical source requiring tens of nanometers wavelength sweep in a few microseconds with a product that increases quadratically with the number of pixels. Fourier domain Mode locked (FDML) lasers can meet these requirements.

The wavelength sweep time $\Delta T$ is equal to the number of pixels n times the time between pulses $\Delta t_i$, governed by the fluorescent decay time $\tau_i$. Considering, for example, 256 horizontal (linescan) pixels and a typical total fluorescent decay time of 10 ns, this time calculates to $\Delta T=2.56$ μs. Assuming a spectral resolution of $\Delta\lambda_i=100$ pm for the diffractive mapping, this means that the light source needs to sweep over $\Delta\lambda=25.6$ nm in $\Delta T=2.56$ μs. A unique feature in SLIDE is that the spectro-temporal bandwidth scales quadratically with the number of pixels (in linescan):

$$\text{Spectro-temporal bandwidth } M_{ST}=\Delta T\times\Delta\lambda= n^2\times\Delta\lambda_i\times\Delta t_i.$$

A wavelength tuning speed of tens of nanometers over few microseconds is beyond the reach of conventional tuneable lasers. Although very fast tuning speeds can be achieved by chirping a supercontinuum pulse source in a dispersive medium as employed in time stretch techniques, achieving a time span of 2.56 μs is about three orders of magnitude beyond the reach of available dispersive elements (typically in the ns-regime). Furthermore, the spreading of energy due to the stretching would result in negligible peak powers and would prevent non-linear excitation.

Spectro-temporal stretch via an FDML laser 12 is the preferred solution for this difficulty. The FDML laser provides a combination of large spectral span along with a time span in microseconds and a narrow instantaneous line width. Its low instantaneous line width allows for diffraction-limited spatial resolution, a feat that is not possible with chirped supercontinuum sources.

In the SLIDE system, the laser 12 is pulse-modulated by an electro-optic modulator (EOM) 14 typically generating 65 ps pulses and amplified to high instantaneous powers sufficient for two photon excitation.

Upon spatial diffraction with diffractive element 22, spectrally swept pulses 20 pump the sample with a unique spatial and temporal sequence 26. The EOM modulation leads to digitally sculpted waveforms 26 making the excitation pattern digitally programmable. Digitally temporal synthesis assigns a unique timing to each pixel. The image is constructed from the time of arrival of the fluorescence signal 28 which is recorded in epi-direction on a hybrid photodetector 30, digitized and processed on a computer controller.

The spectro-temporal imaging with large spectro-temporal bandwidth permits simultaneous single shot Two-Photon excited fluorescence (TPEF) and fluorescence lifetime imaging (2P-FLIM). The current standard for fluorescent lifetime measurement is time-correlated single-photon counting (TCSPC). The inherent drawback with conventional systems is the speed limitation caused by less than one fluorescence photon emission per excitation pulse. The system of FIG. 1 is several orders of magnitude faster than conventional approaches.

The technology described herein may be better understood with reference to the accompanying examples, which are intended for purposes of illustration only and should not be construed as in any sense limiting the scope of the technology described herein as defined in the claims appended hereto.

Example 1

Figure 2:
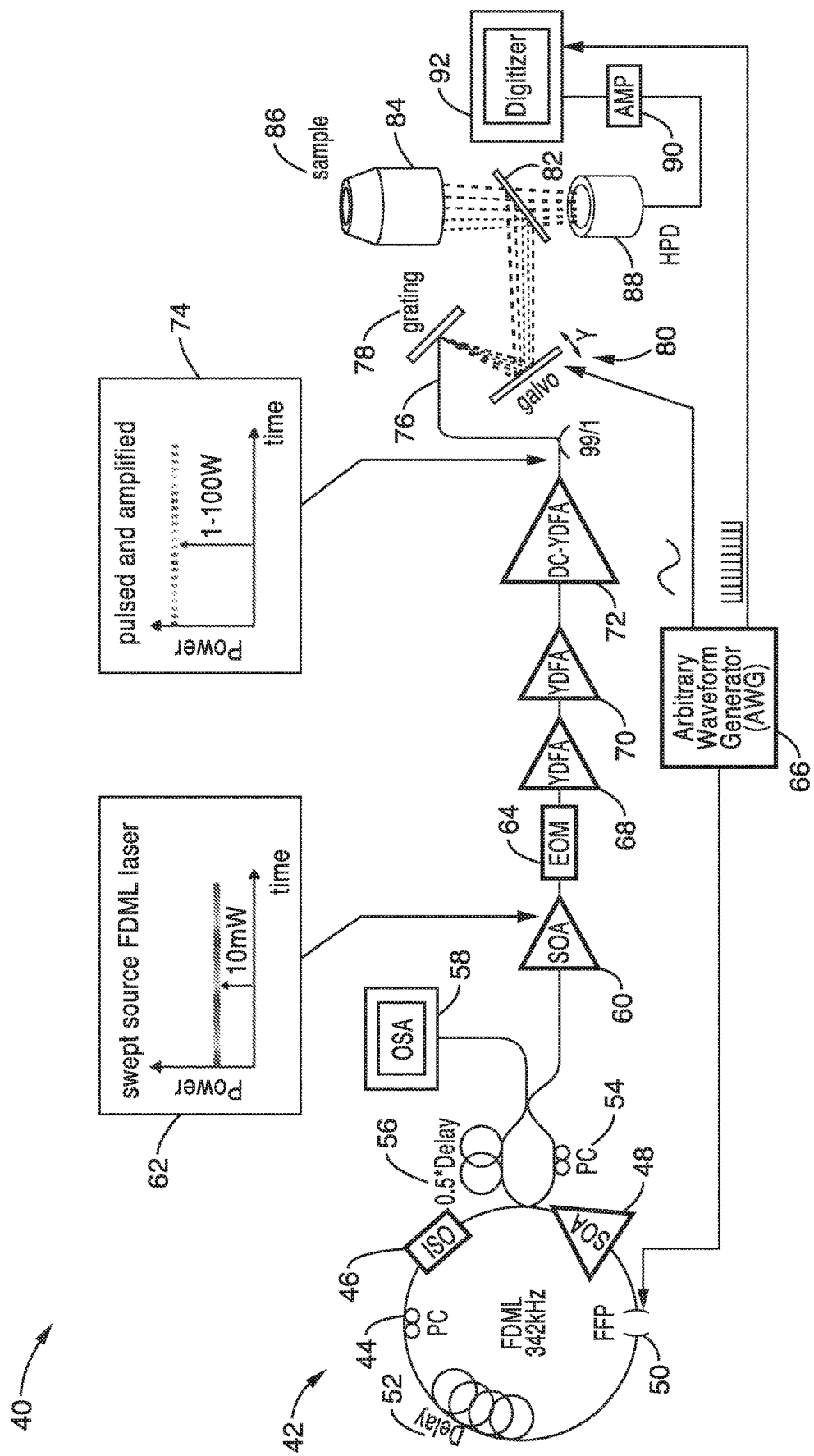
FIG. 2 is a functional block diagram of an alternative embodiment a system for fast two-photon imaging by diffracted swept laser excitation according to the technology.

In order to demonstrate the operational principles of the apparatus and the capture and identification methods, a testing apparatus embodiment was fabricated with a structure and processing steps shown generally in FIG. 2 and tested.

The setup of the Spectro-temporal Lifetime Imaging by digitally sculpted excitation (SLIDE) system embodiment 40 shown if FIG. 2 has a light source 42 with a wavelength swept FDML laser at 1060 nm (±6 nm) and 342 kHz sweep repetition rate. The light source 42 in this embodiment has a PC: Polarization Controller 44, an ISO: Isolator 46, a SOA: semiconductor optical amplifier 48 a FFP: Fiber Fabry-Pérot Filter 50, and a delay 52. The light source output 62 also has a PC: Polarization Controller 54, a delay 56 and an OSA: optical spectrum analyzer 60. The wavelength sweep is accomplished by the fibre Fabry-Pérot-Filter (Lambdaquest) 50 driven at 171 kHz. The FDML output is two-times buffered to 342 kHz sweep rate. After the buffer stage, a booster semiconductor optical amplifier (SOA, Innolume SOA-1060-90-Hi-30 dB) 60 was installed.

In one embodiment, the temperature of the Fiber Fabry-Pérot Filter 50 was controlled to control the phase of the oscillation. As the phase of an oscillator changes dramatically over the frequency at a resonant frequency, the precise control of the frequency was important for the phase control. Here, the frequency is dependent on the temperature so controlling the temperature can be important. The phase of the oscillation was also important, as this determines the instantaneous wavelength output of the wavelength agile light source. When the light source is diffracted on a diffractive element, this phase determines the timing of a specific diffraction angle.

The boosted output was modulated to typically 256 impulses of short temporal width (65 ps) by an electro-optical modulator (EOM) 64. The impulses are digitally synthesized on an arbitrary waveform generator (AWG) 66, which also drives the FDML laser 42. The electronic waveforms for the filter and the 50% modulation of the cavity SOA 60 (same model as in booster stage, driven by a Highland Technologies T160 driver) were programmed on the arbitrary waveform generator 66 (AWG, Tektronix AWG7052).

To enable non-linear excitation, these optical pulses 74 were amplified to high instantaneous powers by two core-pumped ytterbium-doped fibre-amplifiers (YDFAs) 68, 70 and a double-clad power amplifier (DC-YDFA) 72 with a 99/1 tap coupler that serves as monitor port. The 99/1 monitor tap coupler allowed beam monitoring and was also used in reflection mode for beam alignment using sample light reflections.

The electronic pulses 76 can be obtained by differentiating the digital marker outputs of the AWG 66 using a 2.92 mm step-to-impulse converter (Entegra Corp.). The obtained optical pulse length was measured to be 65 ps. The amplitude electro-optical modulator (EOM) 64 was a 20 GHz bandwidth model (Photline NIR-MX-LN-20) that was employed in combination with an electronic pulse amplifier (Multilink MTC5515).

Spectral line-scanning of the pulsed and amplified output 76 was achieved by a diffraction grating 78. The y-axis was scanned by a synchronously driven galvo scanner 80 and controller. The driving signal was also generated on the AWG 66. A high numerical aperture (NA) objective 84 focuses the excitation light on the sample 86 and collects the epi-generated fluorescence signal. A dichroic filter 82 directed only non-linear signals on a fast hybrid photodetector (HPD) 88, connected to a transimpedance amplifier 90 and a fast digitizer/computer 92. Either an oscilloscope (Tektronix DPO71604B) at 3.125 GSamples/s or a streaming ADC card (Innovative Integrations Andale X6GSPS) with synchronously driven sample clock at 3196 MHz were employed s digitizers 92. To ensure sample-accurate fitting, an external sample clock was employed such that the data acquisition runs synchronously to the FDML laser 42 and the pulse modulation. In order to acquire large data sets, a streaming ADC in combination with a RAID-SSD array was employed to store the data and process in post acquisition. The sample clock of the digitizer/computer 92 can also be synchronized to the excitation by a sample clock signal from the AWG 66.

It can be seen that the whole system is driven by the arbitrary waveform generator 66 (AWG, Tektronix AWG7052) and controller. This AWG 66 provides all of the digitally synthesized driving waveforms, driving the FDML laser (Fabry-Perot Filter waveform and 50% modulation of SOA for buffering), the galvo-mirror 80 and also generating an external sample clock signal for the digitizer 92. The waveforms are digitally programmed and enable flexibility on the number of pulses per sweep, pulse pattern and enabling the possibility of warped sampling. For very short lifetimes, a higher repetition rate can be employed.

In one embodiment, the light from the light source was collimated using an f=37 mm lens followed by a beam-expander (f=100 mm and f=150 mm) upon exiting the single-mode fiber 76. This resulted in a beam diameter of 11.5 mm filling the 60× microscope objective aperture 84. The grating 78 was positioned at a 30° angle, such that the first order was reflected at almost the incident direction in order to minimize ellipticity of the first-order diffraction beam. At 1200 lines/mm the grating 78 only produced a 0 and +1 diffraction order and the first order power was maximized by adjusting the polarization on a polarization control paddle. The grating resolution was calculated to be 67 pm. This fits well to the instantaneous line width of the FDML, which was measured for a single pulse to be 56 pm. Considering spectral mapping, the 12 nm FDML span leads to 12 nm/0.067 nm≈180 discernible pixels, which were oversampled using 256 pulses per sweep, i.e. pixels per line. It is important to note that the applied 12 nm sweep span lies well inside most absorption bandwidths.

For TPEF imaging, the excitation can be considered monochromatic. A 12 nm bandwidth calculates to an approximately 140 fs time-bandwidth limited pulse, which is routinely applied for TPM. In fact, even shorter pulses are used, scaling quadratically in bandwidth. Consequently, even larger FDML spans can be applied in this setup, leading to larger scan fields and fields of view (FOVs) in the future. For simplicity, the excitation can thus be considered almost monochromatic. Any spectral considerations of the excitation serve solely for the purpose of fast, inertia-free beam steering, especially since fluorescence excitation characteristic is independent of the exact excitation wavelength.

For microscopy adaptations, two lenses were used to relay image the beams onto a galvanometric mirror (EOPC) 80 for y-axis scanning. The galvo mirror 80 was driven synchronously, producing 170 lines at 2.012 kHz. A high NA, oil immersion microscope objectives 84 was used (Nikon Plan Apo 60× NA 1.4 oil). The field-of-view (FOV) was determined by inserting a resolution target and recording the reflected excitation light on a CCD camera installed in the microscope, which was sensitive to the 1064 nm excitation light. If linearly sampled, the FOV was scanned by a cosine mapping in both axes, so a non-linear mapping is produced. The FOV could be dynamically adjusted using warped sampling or adjusting the swept wavelength and galvo voltages. A dichroic mirror 88 (Thorlabs DMSP950R) in combination with an additional short-pass optical filter (Semrock FF01-750) transmits the Epi-generated signals to a hybrid Photodetector 88 (HPD, Hamamatsu R10467U-40)

with high quantum efficiency (45%). The high time resolution of the HPD 88 in combination with a fast digitizer 92 (~3 GS/s) leads to a fast instrument response function (IRF) of only 1026 μs, measured by detecting the instantaneous signal of SHG in urea crystals.

Example 2

For cell classification and detection of rare cells, such as circulating tumour and fetal cells, it is important to measure a high number of cells quickly, accurately and as non-invasively as possible. Two-photon microscopy has high three dimensional resolution, can operate in blood flow and offers deeper penetration than one-photon techniques through the use of longer wavelengths. Two photon imaging in flow may also be used for non-invasive in vivo cancer cell detection through the skin barrier.

To further illustrate the capabilities of the system, Two-Photon Fluorescence Lifetime Imaging (2P-FLIM) based flow cytometry at an 88 MHz pixel rate was demonstrated. The particles were fluorescent beads used in blood flow determination studies with diameters in the range 2 μm to 15 μm, similar to typical cell sizes. The flow-rate was set to 0.2 m/s, limited by diffraction spot size and fluorescent lifetime.

In the flow cytometry recordings, the flow-rate was set by two fundamental properties, namely the fluorescence lifetime and the imaging diffraction limit. The lifetime limits the repetition rate to approximately 100 MHz, while the diffraction limit is sampled at approximately 380 nm. Consequently, an 88 MHz repetition rate at 256 pulses per 2.92 μs linescan rate was used with a 100 μm field-of-view. The flow rate was equally set to sample each line at 380 nm, i.e. 380 nm/2.92 μs=0.13 m/s. The scale bars in the flow cytometry images were generated using the known 10 μm size of the Red-species bead to calibrate the actual flow speed. The Red bead was sampled with 18 lines, calculating to a line spacing of 556 nm. Using the line scan rate of 342 kHz, this calculates to a flow speed of ~0.2 m/s. At 100 μm field-of view and 10 μm average particle size, this corresponds to the possibility of imaging up to 200,000 particles per second via 2P-FLIM.

The vertical axis was scanned by the SLIDE swept laser scan at 342 kHz line-scanning rate. At 550 nm resolution sampling, the imaging flow-rate was 0.2 m/s. Five different species of blood-flow determination fluorescent beads were imaged and color-coded based on their fluorescent lifetime. The images that were obtained clearly showed the five different species. The fitted lifetimes of the Crimson, Nile Red and Red-Orange beads were clearly distinguishable. Each lifetime curve was taken from a single pixel after a 9×9 box blur filter was applied. The lifetimes of the Red and Orange beads were very close together and were difficult to distinguish by mere lifetime (Ci). However, their different sizes of 10 μm and 15 μm, respectively, were clearly resolved in the lifetime images. Each line was scanned at 2.92 μs, so for a 256×170 image the recording time is only 497 μs. The pixel rate was 88 MHz, i.e. single excitation pulse per pixel without averaging. The power used was 15 mW, scale bars represent 10 μm.

Accordingly, the high-throughput and the combination of different, independent physical information (morphology, fluorescence, lifetime etc.) could be applied to targeted detection of e.g. rare tumour cells in blood or rapid cell sorting at high specificity by intelligently analyzing the features with artificial intelligence and machine learning. By further combining this imaging setup with GPU-based machine learning, this setup can lead to high-speed, high-throughput cell classification and screening.

Example 3

To further demonstrate the capabilities of the system, high speed two photon fluorescent images and fluorescent lifetime images of pollen and algae cells were obtained and evaluated. Fluorescent imaging can be used for classifications of algae cells used in biofuels based on their lipid content. *Euglena gracilis* algae cells with rich lipid content were stained with Nile Red. The cell's chloroplasts provide endogenous autofluorescence and the difference in fluorescent lifetimes clearly highlight the different sub-cellular features. These images were unaveraged and acquired within 497 μs for both TPEF and 2P-FLIM images that were acquired simultaneously. The lifetimes were extracted by de-convolving with the instrument's response function.

For precise measurement, a deconvolution with the IRF was conducted in order to extract the fluorescent lifetimes. However, this was time consuming, so for faster processing and qualitative results a tail-fitting algorithm was used. In some settings, different species need to be discerned so a qualitative value is sufficient.

A direct signal processing approach was conducted, not requiring any fitting and thus being very fast. In the *Euglena* algae cell images, the first 1 ns of the decay signal was integrated and used for the red image channel in order to visualize the rapidly decaying chlorophyll autofluorescence. For the green channel, the Nile Red lipids were visualized by integrating the signal from 2 ns to 8 ns, i.e. later in the decay curve. This resulted in a clear molecular contrast based on fluorescence lifetime. For all images, the data was processed and images created in LabVIEW. The 2P-FLIM images were generated as HSL-images, where Hue was given by the lifetime-values, lightness by the integrated TPEF signal and constant saturation. For the TPEF images, the "Red Hot" look-up table was applied in ImageJ. The plots were generated in GNUPlot and the figures produced using Inkscape.

Two-Photon excited fluorescence (TPEF) image of a pollen grain were obtained with the image size of 512×340 px, pixel-rate 176 MHz, 100-times averaged, 80 mW on the sample. A Two-Photon fluorescence lifetime images (2P-FLIM) were generated from the same data by fitting an exponential decay to the analogue fluorescence decay curve. The autofluorescence reveals different lifetimes for the body and the spikes, which was not visible in the mere TPEF image.

*Euglena gracilis* algae, whose chloroplasts provide autofluorescence were imaged with the lipids stained with Nile Red. The unaveraged image consisted of 256×170 pixels and was acquired within 497 μs (2 kHz frame-rate, 30 mW optical power). The 2P-FLIM revealed differences in fluorescence lifetime based on the molecular environment inside the sample. For all 2P-FLIM images, a 3×3 box blur filter was applied in the time-domain.

Since the fluorescent excitation pattern can be digitally programmed it can adapt to the sample being imaged. Applications of this to foveated (non-uniform) sampling for image compression and to digital zoom were evaluated. By engineering the temporal pulse density, the excitation pixel density can be adapted to the sparsity of the sample.

In one example, high pixel resolution was achieved in the central field of view with lower density in the peripheral vision. Higher resolution by a factor 2.5 could be achieved with same number of pixels. It is important to note that this was achieved through direct non-uniform sampling in contrast to warped (anamorphic) stretch of the image prior to uniform sampling as recently demonstrated. In high-speed imaging, this optical data compression reduces the amount of data generated thereby alleviating the digital processing and storage requirements.

In SLIDE, the excitation pattern can also be digitally sculpted through waveform controlling the wavelength sweep of the FDML laser. It was possible to digitally control the optical zoom for TPEF and 2P-FLIM. Unlike conventional digital zoom, the resolution was not lost at high magnifications.

It was shown that digitally sculpted waveforms enable flexible imaging parameters. For example, the horizontal pixel rate can be reduced to achieve lower average power, while keeping the frame-rate constant. A pixel rate of only 11 MHz was programmed, corresponding to 32 Pixels per line, lowering the average power to 20 mW. When using a linear sampling pattern, the sharp features of the pollen grain were under-sampled. After interpolation the spikes of the pollen grain were almost not visible. However, when programming a foveated warped sampling pattern, a higher sampling density was allotted to the centre of the image. After interpolation, the pollen grain could be nicely resolved even at only 32 horizontal pixels per line. The resolution enhancement in the centre was observed to be 2.5.

Another capability of the system is scale invariant digital optical zoom, which was achieved by digitally decreasing the sweep span of the FDML laser. The TPEF and 2P-FLIM images showing a high-detailed Pollen grain could be more effectively sampled by reducing the spectral span 1.5-fold or 3-fold while maintaining the optical resolution.

From the description herein, it will be appreciated that the present disclosure encompasses multiple embodiments which include, but are not limited to, the following:

1. A laser scanning apparatus, comprising: (a) a wavelength agile laser multi-color light source; (b) a modulator configured for modulating said multi-color light source into a dynamic time pattern; and (c) a diffractive element configured for diffracting said dynamic time pattern of wavelength agile light onto a sample; (d) wherein different wavelengths of light are preferentially diffracted at different angles.

2. The apparatus of any preceding embodiment, wherein the wavelength agile laser light source is a wavelength swept laser.

3. The apparatus of any preceding embodiment, said modulator further comprising: an optical amplifier for amplifying the modulator output to instantaneous powers higher than an average power.

4. The apparatus of any preceding embodiment, wherein said pulse modulator comprises stimulated Raman scattering (SRS) providing both pulse modulation and amplification.

5. The apparatus of any preceding embodiment, wherein the dynamic time pattern of the modulator encodes a diffraction pattern imposed on the sample.

6. The apparatus of any preceding embodiment, wherein the diffractive element comprises a spatially adjustable grating.

7. The apparatus of any preceding embodiment, further comprising: a high numerical aperture lens for focusing diffracted beams on to the sample.

8. The apparatus of any preceding embodiment, further comprising: a detector configured to detect interactions of the dynamic time pattern with the sample; and an imager.

9. The apparatus of any preceding embodiment, further comprising: a controller configured to control laser, modulator, diffractive element and detector functions.

10. The apparatus of any preceding embodiment, wherein the detector is selected from the group of detectors consisting of an avalanche photodetector, a photomultiplier tube, a hybrid photodetector, a multichannel plate, charged coupled detector, a CMOS detector, an arrayed detector, a gated detector, and an image intensifier.

11. The apparatus of any preceding embodiment, wherein an illumination pattern applied to the sample can be dynamically formed by control of one or more of the wavelength outputs of the agile laser, the modulation dynamic time pattern, and an adjustable diffractive element.

12. The apparatus of any preceding embodiment, further comprising: an electro-optical element configured for time modulation; and a time-dependent bias voltage applied to the electro-optical element by the controller to match a wavelength dependent bias voltage to the instantaneous color output of the wavelength agile laser.

13. A laser scanning apparatus, comprising: (a) a wavelength swept laser configured for generating a broadband light source; (b) a pulse modulator configured for modulating said broadband light source into short pulses; and (c) a diffraction grating configured for diffracting said wavelength swept short pulses into a spectral brush directed onto a line or a two-dimensional array on a sample; and (d) a detector configured to detect interactions of the spectral brush with the sample; (e) wherein each of said short pulses are diffracted at a different angle in response to their differing wavelength inducing a pixel wise interaction with the sample.

14. The apparatus of any preceding embodiment, further comprising: an optical amplifier for amplifying the short pulses.

15. The apparatus of any preceding embodiment, further comprising: an adjustable beam scanner configured to direct beams from the diffraction grating to the sample.

16. The apparatus of any preceding embodiment, further comprising: a high numerical aperture lens for focusing diffracted beams from the beam scanner on to the sample.

17. The apparatus of any preceding embodiment, further comprising: a controller configured to control laser, modulator, diffractive element, beam scanner and detector functions.

18. The apparatus of any preceding embodiment, wherein the wavelength swept laser is controlled with an electronic waveform from the controller to produce a linear wavelength sweep.

19. The apparatus of any preceding embodiment, wherein the wavelength swept laser is controlled with an electronic waveform from the controller to produce a k-space linear frequency sweep.

20. The apparatus of any preceding embodiment, wherein detection by the detector is synchronized with the pulse modulation by the controller to only detect signals generated synchronously with the applied pulses thereby suppressing any background signals.

21. The apparatus of any preceding embodiment, wherein the modulator is operated by the controller with both a pulse pattern and a sweep pattern to improve modulation depth of the pulses.

22. The apparatus of any preceding embodiment, wherein a non-linear interaction comprising the simultaneous absorption of two or more photons is induced at the sample.

23. The apparatus of any preceding embodiment, wherein a digitally sculpted waveform is applied to the pulse modulation of the modulator by the controller to produce non-uniform sampling of the sample.

24. The apparatus of any preceding embodiment, wherein said interaction detected by the detector is selected from the group consisting of absorption, non-linear absorption, reflection, scattering, ionization, plasma formation, polymerization, lithography, ablation, spectroscopy, and laser induced breakdown spectroscopy.

25. The apparatus of any preceding embodiment, further comprising: a flow apparatus where objects pass the optical beam in flow; wherein fluorescence lifetime imaging is performed of the objects in flow.

26. The apparatus of any preceding embodiment, further comprising an imager operably coupled to the detector.

27. The apparatus of any preceding embodiment, wherein individual pulse length, repetition rate, pulse pattern, individual pulse height and individual pulse form of the broadband light source are controlled by the controller.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A laser scanning apparatus, comprising:
   (a) a wavelength agile laser multi-color light source;
   (b) a modulator configured for modulating said multi-color light source into a dynamic time pattern; and
   (c) a diffraction grating configured for diffracting said dynamic time pattern of wavelength agile light onto a sample;
   (d) wherein different wavelengths of light are preferentially diffracted at different angles.

2. The apparatus of claim 1, wherein the wavelength agile laser light source is a wavelength swept laser.

3. The apparatus of claim 1, said modulator further comprising:
   an optical amplifier for amplifying the modulator output to instantaneous powers higher than an average power.

4. The apparatus of claim 1, wherein said modulator comprises stimulated Raman scattering (SRS) providing both pulse modulation and amplification.

5. The apparatus of claim 1, wherein the dynamic time pattern of the modulator encodes a diffraction pattern imposed on the sample.

6. The apparatus of claim 1, wherein the diffraction grating comprises a spatially adjustable grating.

7. The apparatus of claim 1, further comprising:
   an objective lens for focusing diffracted beams on to the sample.

8. The apparatus of claim 1, further comprising:
   a detector configured to detect interactions of the dynamic time pattern with the sample; and
   an imager.

9. The apparatus of claim 1, further comprising:
   a controller configured to control laser, modulator, diffraction grating and detector functions.

10. The apparatus of claim 9, wherein an illumination pattern applied to the sample can be dynamically formed by control of one or more of the wavelength outputs of the agile laser, the modulation dynamic time pattern, and an adjustable diffraction grating.

11. The apparatus of claim 9, further comprising:
    an electro-optical modulator configured for time modulation; and
    a time-dependent bias voltage applied to the electro-optical modulator by the controller to match a wavelength dependent bias voltage to the instantaneous color output of the wavelength agile laser.

12. The apparatus of claim 1, wherein the detector is selected from the group of detectors consisting of an avalanche photodetector, a photomultiplier tube, a hybrid photodetector, a multichannel plate, charged coupled detector, a CMOS detector, an arrayed detector, a gated detector, and an image intensifier.

13. A laser scanning apparatus, comprising:
    (a) a wavelength swept laser configured for generating a broadband light source;
    (b) a pulse modulator configured for modulating said broadband light source into short pulses; and
    (c) a diffraction grating configured for diffracting said wavelength swept short pulses into a spectral brush directed onto a line or a two-dimensional array on a sample; and
    (d) a detector configured to detect interactions of the spectral brush with the sample;
    (e) wherein each of said short pulses are diffracted at a different angle in response to their differing wavelength inducing a pixel wise interaction with the sample.

14. The apparatus of claim 13, further comprising:
    an optical amplifier for amplifying the short pulses.

15. The apparatus of claim 13, further comprising:
    an adjustable beam scanner configured to direct beams from the diffraction grating to the sample.

16. The apparatus of claim 15, further comprising:
    an objective lens for focusing diffracted beams from the beam scanner on to the sample.

17. The apparatus of claim 16, wherein individual pulse length, repetition rate, pulse pattern, individual pulse height and individual pulse form of the broadband light source are controlled by the controller.

18. The apparatus of claim 15, further comprising:
    a controller configured to control laser, modulator, diffractive element, beam scanner and detector functions.

19. The apparatus of claim 18, wherein the wavelength swept laser is controlled with an electronic waveform from the controller to produce a linear wavelength sweep.

20. The apparatus of claim 18, wherein the wavelength swept laser is controlled with an electronic waveform from the controller to produce a k-space linear frequency sweep.

21. The apparatus of claim 18, wherein detection by the detector is synchronized with the pulse modulation by the controller to only detect signals generated synchronously with the applied pulses thereby suppressing any background signals.

22. The apparatus of claim 18, wherein the modulator is operated by the controller with both a pulse pattern and a sweep pattern to improve modulation depth of the pulses.

23. The apparatus of claim 18, wherein a digitally sculpted waveform is applied to the pulse modulation of the modulator by the controller to produce non-uniform sampling of the sample.

24. The apparatus of claim 13, wherein a non-linear interaction comprising the simultaneous absorption of two or more photons is induced at the sample.

25. The apparatus of claim 13, wherein said interaction detected by the detector is selected from the group consisting of absorption, non-linear absorption, reflection, scattering, ionization, plasma formation, polymerization, lithography, ablation, spectroscopy, and laser induced breakdown spectroscopy.

26. The apparatus of claim 13, further comprising:
a plate with at least one fluidic channel with a fluidic flow where sample objects pass the optical beam in flow;
wherein fluorescence lifetime imaging is performed of the objects in flow.

27. The apparatus of claim 13, further comprising an imager operably coupled to the detector.

* * * * *